US00PP10957P

United States Patent [19]

Bull

[11] Patent Number: Plant 10,957

[45] Date of Patent: Jun. 15, 1999

[54] NEW GUINEA IMPATIENS PLANT NAMED 'MARLEN'

[76] Inventor: Norbert Bull, Gaertnersiedlung 2, 24610 Goennebeck, Germany

[21] Appl. No.: 08/881,082

[22] Filed: Jun. 23, 1997

[30] Foreign Application Priority Data

Nov. 20, 1996 [DE] Germany ..... IM 415

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 7,838 3/1992 Kientzler ..... Plt./87.6

P.P. 8,360 8/1993 Bull ..... Plt./87.6

OTHER PUBLICATIONS

GTITM UPOVROM Citation for 'Marlen' as per DE PBR IM 00415, Jan. 15, 1997.

*Primary Examiner*—Howard J. Locker
*Assistant Examiner*—Kent L. Bell
*Attorney, Agent, or Firm*—Foley & Lardner

[57] ABSTRACT

A new and distinct cultivar of New Guinea Impatiens plant named 'Marlen', characterized by its salmon pink flower with small red eye, medium sized flowers, medium green foliage, compact plant habit, and medium spring flowering response.

1 Drawing Sheet

The present invention comprises a new and distinct cultivar of New Guinea Impatiens, referred to by the cultivar name 'Marlen'.

'Marlen' is a product of a planned breeding program and was originated from a hybridization made by the inventor Norbert Bull in a controlled breeding program in Goennebek, Germany, in 1993. The female parent was a seedling designated No. 24 and the male parent was a seedling designated No. 2. Both parents are proprietary cultivars used in the breeding program.

'Marlen' was discovered and selected as one flowering plant within the progeny of the stated cross by the inventor in 1994 in a controlled environment in Goennebek, Germany.

The first act of vegetative or asexual reproduction of 'Marlen' was accomplished when cuttings were taken from the initial selection in Autumn 1994 in a controlled environment in Goennebek, by, or under the supervision of, Norbert Bull.

Horticultural examination of plants grown from cuttings of the clone initiated in Spring 1995 in Goennebek, Germany, and continuing thereafter, has demonstrated that the combination of characteristics as herein disclosed for 'Marlen' are firmly fixed and are retained through successive generations of asexual reproduction.

'Marlen' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Marlen' which in combination distinguish this New Guinea Impatiens as a new and distinct cultivar:

1. Salmon pink flowers color with a small red eye.
2. Medium sized flowers.
3. Medium green foliage.
4. Compact plant habit.

5. Medium spring flowering response.
6. Resistant to powdery mildew.

Of the many commercial cultivars known to the present inventor, the most similar in comparison to 'Marlen' are the commercial variety 'Barbara' (unpatented) and the cultivar 'Delias', the latter being disclosed in U.S. Plant Pat. No. 7,838.

In comparison to 'Barbara', the flowers of 'Marlen' have a less distinct dark red eye, its leaves have pink veins in contrast to the red veining of 'Barbara', and 'Marlen' has a more compact growth habit.

In comparison to 'Delias', 'Marlen' has a different salmon flower color, slightly different shape of corolla, and a shorter plant habit.

The accompanying photographic drawing shows typical flower and foliage characteristics of 'Marlen', with colors being as true as possible with illustrations of this type. In this regard, the illustration may not depict the color designations and descriptions as they accurately appear in the botanical description. The lighting is bright as to give the appearance of lighter, less-intense hues.

In the following description color references are made to The Royal Horticultural Society Color Chart.

The color values were determined indoors from flowers taken from plants grown in Hillscheid, Federal Republic of Germany, under greenhouse conditions which approximate those generally used in commercial practice.

The description is based on plants which were planted as rooted cuttings in 10 cm pots in early March and grown at 20° C. minimum temperature.

Classification:

*Botanical.*—A hybrid of the genus Impatiens.
*Commercial.*—New Guinea Impatiens cv. 'Marlen'.

I. PLANT

A. General appearance and form:

*Habit.*—Compact, uniformly molded, round, well branched, and growth is indeterminate, although weak after flowering begins.

*Height.*—11 cm.
*Width.*—25 cm.
*Internode length.*—15–30 mm.
*Stem color.*—Green, with light red lining.
*Flowering response.*—8–9 weeks after planting of rooted cuttings.
*Flowering season.*—Generally indeterminate, mainly from March to October, depending on light intensity.
*Propagation.*—Usually terminal tips for cuttings.
*Rooting.*—Color is R.H.S. 159B-C; roots initiate in about 18 days at 22° C., from sticking to transplanting.

Foliage:
*Leaf arrangement.*—Primarily in whorls, which are tight and rosette-like.
*Shape of leaf.*—Narrow ovate to elliptic, with acute base and acute or slightly acuminate tip.
*Margin.*—Slightly serrated, ciliated.
*Leaf, length.*—About 110 mm.
*Leaf, width.*—About 38–42 mm.
*Main color of upper surface.*—Light medium green, approximately R.H.S. 137B-C.
*Veins on upper surface, color.*—Very light brownish pink near the base of leaf, about R.H.S. 48B or lighter, fading to light green toward the tip of the leaf.
*Variegation on leaf.*—Absent.
*Main color of lower surface.*—Light green, about R.H.S. 138B.
*Veins on lower surface, color.*—Mainly greenish-white, occasionally slight infusion of anthocyanin.
*Petiole, color.*—Light green, pink lined.
*Petiole, length.*—About 5–10 mm.

II. INFLORESCENCE

A. FLOWER:
*Flower number per node.*—Floriferous, up to 8 in various stages of development, often more than one flower per leaf.
*Form of corolla.*—Single.
*Shape.*—Slightly zygomorph, upper petal cupped.
*Average length.*—58 mm.
*Average width.*—55 mm.
*Color (general tonality from a distance of three meters).*—Salmon pink R.H.S. 55A for younger florets, which may fade to R.H.S. 55A-B after pollen is shed.
*Petal number.*—Five (5).
*Petal shape.*—Roughly heart-shaped, moderately lobed, upper petal slightly cupped in immature plant.
*Petal length.*—27–29 mm.
*Petal width.*—Upper petals are about 35–40 mm and lower petals are about 28–32 mm.
*Petal texture.*—Smooth, slightly glossy.
*Main color of upper surface.*—R.H.S. 55A.
*Color of lower surface.*—R.H.S. 55A.
*Eye zone.*—Small, dark red R.H.S. 57A.
*Spur, color.*—R.H.S. 53D or lighter.
*Spur shape and size.*—Downwardly curved, about 45 mm in length.
*Pedicel, length.*—About 26–30 mm.
*Pedicel, color.*—Brownish pink, about R.H.S. 180B.

III. REPRODUCTIVE ORGANS

Androecium:
*Stamens.*—Five (5) in number, fused, upper surface color is mainly R.H.S. 46C.
*Anthers.*—Hooded, color is about R.H.S. 11D.
*Pollen.*—Color is about R.H.S. 4D.

Gynoecium:
*Stigma and style.*—Five (5) in number, very short, color is about R.H.S. 11D.
*Ovary.*—Five (5) celled, 3–5 mm in length, surface color is R.H.S. 137B.

I claim:

1. A new and distinct cultivar of New Guinea Impatiens plant named 'Marlen', as illustrated and described.

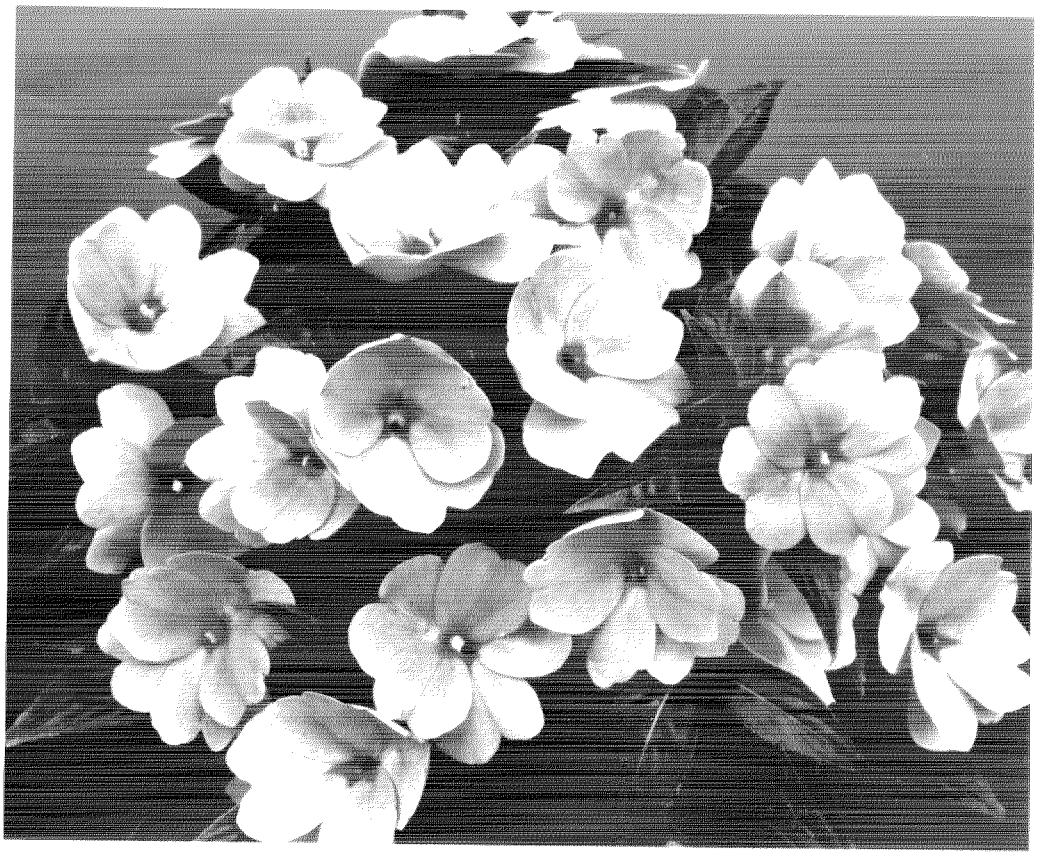

* * * * *